United States Patent [19]
Bandman et al.

[11] Patent Number: 5,972,658
[45] Date of Patent: Oct. 26, 1999

[54] DNA ENCODING LUNG GROWTH FACTOR VARIANT

[75] Inventors: Olga Bandman, Mountain View; Surya K. Goli, Sunnyvale; Lynn E. Murry, Portola Valley, all of Calif.

[73] Assignee: Incyte Pharmaceuticals, Inc., Palo Alto, Calif.

[21] Appl. No.: 08/760,745

[22] Filed: Dec. 5, 1996

[51] Int. Cl.⁶ .............................. C12N 15/00; C12N 1/21; C12N 1/15; C07H 21/04
[52] U.S. Cl. ................ 435/69.4; 435/252.3; 435/254.11; 435/419; 435/320.1; 536/23.51
[58] Field of Search ................................ 435/69.4, 252.3, 435/254.11, 419, 320.1; 536/23.51

[56] References Cited

U.S. PATENT DOCUMENTS 5,235,042  8/1993  Klagsbrun .............................. 530/399

FOREIGN PATENT DOCUMENTS 06343470  12/1994  Japan .

OTHER PUBLICATIONS

Adams, M.D. et al, HS20113, "EST28619 *Homo sapiens* cDNA" EMBL Sequence Database, Sep. 8, 1995, Heidelberg, Germany.

George et al. Current methods in sequence comparison and analysis. In: Macromolecular Sequencing and Synthesis (DH Schlesinger, ed.) Alan R. Liss, Inc., NY, pp. 127–149, 1988.

Nakamura, H. et al., "Molecular cloning of complementary DNA for a novel human hepatoma–derived growth factor. Its homology with high mobility group–1 protein.", *J.Biol.Chem.* (1994) 269(40):25143–25149.

Baxevanis, A.D., et al., "The HMG–1 box protein family: classification and functional relationships.", *Nucleic Acids Res.* (1995) 23(9):1604–1613.

Morton, R.L., et al., "Chromosomal proteins HMG–14 and HMG–17 are synthesized throughout the S–phase in Burkitt's lymphoma.", *Biochem.Biophys.Res.Commun.* (1996) 222(2):368–373.

Harley, V.R., et al., "The HMG box of SRY is a calmodulin binding domain.", *FEBS Lett.* (1996) 391(1–2):24–28.

Onate, S.A. et al., "The DNA–bending protein HMG–1 enhances progesterone receptor binding to its target DNA sequences.", *Mol.Cell Biol.* (1994) 14(5):3376–3391.

Izumoto, Y. (Direct Submission), GenBank Sequence Database (Accession 945419), National Center for Biotechnology Information, National Library of Medicine, Bethesda, Maryland, 20894.

Auffray et al. *H.sapiens* partial cDNA sequence; clone c–10e06. EST–STS Accession No. Z43004, Sep. 21 1995.

Charnock–Jones et al. Extension of incomplete cDNAs (ESTs) by biotin/streptavidin–mediated walking using the polymerase chain reaction. Journal of Biotechnology. vol. 35, Nos. 2–3, pp. 205–215. Jun. 30, 1994.

Liew. J2942F *Homo sapiens* cDNA clone J2942 5 similar to Hepatoma–Derived Growth Factor. EST–STS Accession No. N85236, Apr. 1, 1996.

Sambrook et al. Moelcular Cloning: A Laboratory Manual, 2d ed. CSHL Press, Cold Spring Harbor, NY. pp. 9.50–.51, 1989.

Adams et al., EST03319 *Homo sapiens* cDNA clone HFBCW96. EST–STS database Accession No. T05430, Jun. 30, 1993.

*Primary Examiner*—Elizabeth C. Kemmerer
*Assistant Examiner*—David S. Romeo
*Attorney, Agent, or Firm*—Lucy J. Billings; Sheela Mohan-Peterson; Incyte Pharmaceuticals, Inc.

[57] ABSTRACT

The present invention provides a human lung growth factor variant (LGFV) and polynucleotides which identify and encode LGFV. The invention also provides genetically engineered expression vectors and host cells comprising the nucleic acid sequences encoding LGFV and a method for producing LGFV. The invention also provides for agonists, antibodies, or antagonists specifically binding LGFV, and their use, in the prevention and treatment of diseases associated with expression of LGFV. Additionally, the invention provides for the use of antisense molecules to polynucleotides encoding LGFV for the treatment of diseases associated with the expression of LGFV. The invention also provides diagnostic assays which utilize the polynucleotide, or fragments or the complement thereof, and antibodies specifically binding LGFV.

8 Claims, 9 Drawing Sheets

```
                9              18             27              36             45             54
5'    C  CGC TGC AGC CGC TTT CTG CGG CCT GGG CCT CTC GCC GTC AGC ATG CCA CAC
                                                                    M   P   H 63              72             81              90             99            108
      GCC TTC AAG CCC GGG GAC TTG GTG TTC GCT AAG ATG AAG GGC TAC CCT CAC TGG
       A   F   K   P   G   D   L   V   F   A   K   M   K   G   Y   P   H   W 117             126            135             144            153            162
      CCT GCC AGG ATC GAC GAC ATC GCG GAT GGC GCC GTG AAG CCC CCA CCC AAC AAG
       P   A   R   I   D   D   I   A   D   G   A   V   K   P   P   P   N   K 171             180            189             198            207            216
      TAC CCC ATC TTT TTC TTT GGC ACA CAC GAA ACA GCC TTC CTG GGC CCC AAA GAC
       Y   P   I   F   F   F   G   T   H   E   T   A   F   L   G   P   K   D 225             234            243             252            261            270
      CTC TTC CCT TAC GAG GAA TCC AAG GAG AAG TTT GGC AAG CCC AAC AAG AGG AAA
       L   F   P   Y   E   E   S   K   E   K   F   G   K   P   N   K   R   K 279             288            297             306            315            324
      GGG TTC AGC GAG GGG CTG TGG GAG ATC GAG AAC AAC CCT ACT GTC AAG GCT TCC
       G   F   S   E   G   L   W   E   I   E   N   N   P   T   V   K   A   S 333             342            351             360            369            378
      GGC TAT CAG TCC TCC CAG AAA AAG AGC TGT GTG GAA GAG CCT GAA CCA GAG CCC
       G   Y   Q   S   S   Q   K   K   S   C   V   E   E   P   E   P   E   P 387             396            405             414            423            432
      GAA GCT GCA GAG GGT GAC GGT GAT AAG AAG GGG AAT GCA GAG GGC AGC AGC GAC
       E   A   A   E   G   D   G   D   K   K   G   N   A   E   G   S   S   D 441             450            459             468            477            486
      GAG GAA GGG AAG CTG GTC ATT GAT GAG CCA GCC AAG GAG AAG AAC GAG AAA GGA
       E   E   G   K   L   V   I   D   E   P   A   K   E   K   N   E   K   G 495             504            513             522            531            540
      GCG TTG AAG AGG AGA GCA GGG GAC TTG CTG GAG GAC TCT CCT AAA CGT CCC AAG
       A   L   K   R   R   A   G   D   L   L   E   D   S   P   K   R   P   K 549             558            567             576            585            594
      GAG GCA GAA AAC CCT GAA GGA GAG GAG AAG GAG GCA GCC ACC TTG GAG GTT GAG
       E   A   E   N   P   E   G   E   E   K   E   A   A   T   L   E   V   E 603             612            621             630            639            648
      AGG CCC CTT CCT ATG GAG GTG GAA AAG AAT AGC ACC CCC TCT GAG CCC GGC TCT
       R   P   L   P   M   E   V   E   K   N   S   T   P   S   E   P   G   S 657             666            675             684            693            702
      GGC CGG GGG CCT CCC CNN NNN NNN NNN NNN NNN NNN NNN NNN NAG GAA GAG GCT
       G   R   G   P   P   X   X   X   X   X   X   X   X   X   X   E   E   A
```

FIGURE 1 A

```
        711         720         729         738         747         756
ACC AAG GAA GAT GCT GAG GCC CCA GGC ATC AAG AGT CAT GAG AGC CTG TAG CCA
T   K   E   D   A   E   A   P   G   I   K   S   H   E   S   L 765         774         783         792         801         810
CCA ATG TTT CAA GAG GAG CCC CCA CCC TGT TCC TGC TGC TGT CTG GGT GCT ACT 819         828         837         846         855         864
GGG GAA ACT GGC CAT GGG CTG CAA ACT GGG NAC CCC TTT TCC ANC NCA ANC TGN

TNT TCT T 3'
```

```
    1 CCGGCTGCAGCCCGCTTTCTGCGGCCTGGGCTCTTCGCCCGTC n876242
    1 ATGTCGCGA------------------TCCAACCCGGC g598956

41 AGCATGCCACACGCCTTCAAGCCCTTGGACTTGGTGTTCG n876242
   20 AGAAGGA-GTACCCCTACTGCCCGGGGGGACTGTGTTCG g598956

81 CTAAAGATGAAGGGGCCTACCCTCACTCAGGATCGAA n876242
   53 CCAAAGATGAAGGGCCTACCCACTCACTCGGATTGA g598956

121 CGACACATCGGCGGATGGGCCCTGCCCCAAACAAAG n876242
   93 CGATGCCTGAGGCTGTGTGAAATCCCAAGAAA g598956

161 TACCCCATCTCTTTTTGGCACACGAAACCCTTCC n876242
  133 TACCCAAGTCTTTTTCGACACGGAGACGGCATTCC g598956

201 TGGGCCCCAAACCTTCTCTTTTCCAACATCCAAGGA n876242
  173 TGGGCCAAACCTCTCTTTTCCAAGACAATCCAAGGA g598956

241 GAAAGTTTCAAAGAAAAAAAAAAACAAACGGGTTCAAAG n876242
  213 GAAGTTCAAACAAGAAACAAACCCGGGTTTCAAAG g598956

281 GGGCTGTCCTTATCCAACCCCCCTTAAGAGCCGAG n876242
  253 GGGTGTCCTATCACCCCCCCCTACTAGACCGAG g598956

321 CCCCGGGGGCCTAAAACCCCAAAACAAGCTGCAGCCCGAA n876242
  293 CCCCCGGGGCCCTTGAAAACAAAGCTGCAGCAGCCGAG g598956

361 GCCCTGAAAAGGGGCAGAATGCCAGCCTGATT n876242
  333 GCCCTGAAAAGGGGGCAGAATGCTGACTGAT g598956

401 AAGAAAAGGGGGCAGAGCAGCCCAAGGGACGAA n876242
  373 AAGAAAGGGGGCAGACAGCCAAGGAGACGGA g598956

441 AGCTGGTCATTGATGAGCCCAAGCCAAGGAGAAA n876242
  413 AGCTGGTCATTGATGAGCCAGCAAGGAGAGAA g598956
```

FIGURE 3B

| Library | Lib Description | Abun | Pct Abun |
|---|---|---|---|
| HNT3AZT01 | hNT2 cell line, teratocarcinoma, treated AZ | 5 | 0.3425 |
| THP1PLB02 | THP-1 promonocyte cell line, treated PMA, LPS | 4 | 0.1630 |
| THP1PEB01 | THP-1 promonocyte cell line, treated PMA | 3 | 0.1463 |
| PANCDIT03 | pancreas, NIDDM, 57 M | 1 | 0.1462 |
| THP1T7T01 | THP1 cells, untreated | 3 | 0.1447 |
| BSTMNOT01 | brain stem, 72 M | 1 | 0.1214 |
| PROSTUT12 | prostate tumor, 65 M, match to PROSNOT20 | 4 | 0.1118 |
| HUVESTB01 | HUVEC endothelial cell line, shear stress | 3 | 0.1078 |
| PENITUT01 | penis tumor, carcinoma, 64 M | 4 | 0.1066 |
| AMLBNOT01 | AML blast cells, blast crisis, 58 F | 1 | 0.1058 |
| COLNNOT13 | colon, ascending, 28 M | 3 | 0.0932 |
| HUVENOB01 | HUVEC endothelial cell line, control | 2 | 0.0841 |
| UTRSNOT05 | uterus, 45 F | 3 | 0.0834 |
| SINTNOT13 | small intestine, ileum, ulcerative cholitis, 25 F | 3 | 0.0826 |
| LUNGTUT03 | lung tumor, 69 M, match to LUNGNOT15 | 5 | 0.0796 |
| OVARNOM01 | ovary, 49 F, WM | 1 | 0.0752 |
| PLACNOM02 | placenta, neonatal F, NORM, WM | 13 | 0.0722 |
| PROSNOT01 | prostate, 78 M | 2 | 0.0702 |
| SPLNFEM01 | spleen, fetal, WM | 2 | 0.0663 |
| COLNNOT19 | large intestine, cecum, 18 F | 2 | 0.0585 |
| PROSTUT05 | prostate tumor, 69 M, match to PROSNOT07 | 4 | 0.0580 |
| COLNFET02 | colon, fetal F | 4 | 0.0571 |
| THP1NOT01 | THP1 cells, untreated | 1 | 0.0571 |
| LUNGTUT02 | lung tumor, metastasis, 79 M, match to LUNGNOT03 | 3 | 0.0567 |
| SININOT01 | small intestine, ileum, 4 F | 2 | 0.0560 |
| THP1AZT01 | THP-1 promonocyte cell line, treated AZ | 1 | 0.0554 |
| LUNGNOT15 | lung, 69 M, match to LUNGTUT03 | 2 | 0.0553 |
| LIVRFET02 | liver, fetal F | 2 | 0.0550 |
| KERANOT02 | keratinocytes, primary cell line, 30 F | 3 | 0.0546 |
| PROSTUT09 | prostate tumor, 66 M | 2 | 0.0529 |
| LEUKNOT03 | white blood cells, 27 F | 2 | 0.0523 |
| TESTNOT03 | testis, 37 M | 4 | 0.0515 |
| COLNPOT01 | colon polyp, 40 F | 2 | 0.0513 |
| PROSNOT14 | prostate, 60 M, match to PROSTUT08 | 2 | 0.0512 |
| BRAITUT02 | brain tumor, metastasis, 58 M | 3 | 0.0509 |
| BRSTTUT03 | breast tumor, 58 F, match to BRSTNOT05 | 5 | 0.0493 |
| TESTNOT01 | testis, 37 M | 1 | 0.0478 |
| UCMCNOT02 | mononuclear cells | 2 | 0.0471 |
| THP1PLB01 | THP-1 promonocyte cell line, treated PMA, LPS | 1 | 0.0452 |
| BRSTNOT02 | breast, 55 F, match to BRSTTUT01 | 4 | 0.0443 |
| PROSNOT02 | prostate, 50 M, match to PROSTUT01 | 1 | 0.0435 |
| COLNNOT08 | colon, 60 M | 1 | 0.0426 |
| PANCTUT02 | pancreatic tumor, carcinoma, 45 F | 2 | 0.0403 |
| SCORNOT01 | spinal cord, 71 M | 2 | 0.0402 |
| UTRSNOT01 | uterus, 59 F | 1 | 0.0394 |
| SINTTUT01 | small intestine tumor, ileum, 42 M | 1 | 0.0382 |
| TLYMNOR01 | lymphocytes (non-adher PBMNC), 24 M, RP | 1 | 0.0379 |
| HNT2RAT01 | hNT2 cell line, teratocarcinoma, treated RA | 2 | 0.0376 |
| BRAINOT03 | brain, 26 M | 2 | 0.0371 |

FIGURE 5A

| | | | |
|---|---|---|---|
| LUNGNOT04 | lung, 2 M | 2 | 0.0366 |
| PROSNOT20 | prostate, 65 M, match to PROSTUT12 | 1 | 0.0336 |
| CARDFEM01 | heart, fetal, NORM, WM | 3 | 0.0335 |
| OVARTUT01 | ovarian tumor, 43 F, match to OVARNOT03 | 1 | 0.0323 |
| OVARNOT02 | ovary, 59 F | 1 | 0.0316 |
| NEUTGMT01 | granulocytes, periph blood, M/F, treated GM-CSF | 2 | 0.0313 |
| BRSTNOT05 | breast, 58 F, match to BRSTTUT03 | 2 | 0.0309 |
| STOMNOT02 | stomach, 52 M, match to STOMTUT01 | 1 | 0.0308 |
| BRSTNOT07 | breast, 43 F | 1 | 0.0307 |
| STOMNOT01 | stomach, 55 M | 1 | 0.0303 |
| LUNGNOT18 | lung, 66 F | 1 | 0.0298 |
| TONGTUT01 | tongue tumor, carcinoma, 36 M | 1 | 0.0295 |
| BRAITUT08 | brain tumor, astrocytoma, 47 M | 2 | 0.0293 |
| COLNTUT06 | large intestine, cecal tumor, 45 F | 1 | 0.0293 |
| LIVSFEM02 | liver/spleen, fetal M, NORM, WM | 11 | 0.0290 |
| BEPINOT01 | bronchial epithelium, primary cell line, 54 M | 2 | 0.0289 |
| PANCNOT07 | pancreas, fetal M | 1 | 0.0287 |
| UTRSNOT06 | uterus, myometrium, 50 F | 1 | 0.0282 |
| LUNGNOT12 | lung, 78 M | 1 | 0.0278 |
| TESTTUT02 | testicular tumor, 31 M | 1 | 0.0278 |
| THYRTUT03 | thyroid tumor, benign, 17 M | 1 | 0.0276 |
| LATRTUT02 | heart tumor, myoma, 43 M | 2 | 0.0275 |
| BEPINON01 | bronchial epithelium, 1° cell line, 54 M, NORM | 1 | 0.0274 |
| OVARNOT07 | ovary, 28 F | 1 | 0.0269 |
| PTHYTUM01 | parathyroid tumor, adenoma, M/F, NORM, WM | 1 | 0.0268 |
| KIDNTUT01 | kidney tumor, Wilms, 8m F | 1 | 0.0267 |
| LATRNOT01 | heart, left atrium, 51 F | 1 | 0.0266 |
| PROSTUT08 | prostate tumor, 60 M, match to PROSNOT14 | 1 | 0.0266 |
| BRSTNOM01 | breast, F, NORM, WM | 1 | 0.0264 |
| BRAITUT13 | brain tumor, meningioma, 68 M | 1 | 0.0262 |
| DUODNOT02 | small intestine, duodenum, 8 F | 1 | 0.0262 |
| URETTUT01 | ureter tumor, 69 M | 1 | 0.0262 |
| BRAITUT07 | brain tumor, left frontal, 32 M | 1 | 0.0259 |
| LIVRTUT01 | liver tumor, metastasis, 51 F | 1 | 0.0259 |
| PROSNOT18 | prostate, 58 M | 1 | 0.0256 |
| PANCNOT08 | pancreas, 65 F, match to PANCTUT01 | 1 | 0.0254 |
| BLADTUT04 | bladder tumor, 60 M, match to BLADNOT05 | 2 | 0.0253 |
| PLACNOB01 | placenta, neonatal F | 1 | 0.0251 |
| LUNGNOT02 | lung, 47 M | 1 | 0.0246 |
| TMLR3DT02 | lymphocytes (non-adher PBMNC), M/F, 72-hr MLR | 1 | 0.0246 |
| HIPONOT01 | brain, hippocampus, 72 F | 1 | 0.0239 |
| RATRNOT02 | heart, right atrium, 39 M | 1 | 0.0237 |
| MMLR1DT01 | macrophages (adher PBMNC), M/F, 24-hr MLR | 1 | 0.0236 |
| TMLR3DT01 | lymphocytes (non-adher PBMNC), M, 96-hr MLR | 1 | 0.0229 |
| PROSNOT06 | prostate, 57 M, match to PROSTUT04 | 2 | 0.0228 |
| LIVRNOT01 | liver, 49 M | 1 | 0.0198 |
| COLNTUT03 | colon tumor, 62 M, match to COLNNOT16 | 1 | 0.0196 |
| CRBLNOT01 | brain, cerebellum, 69 M | 1 | 0.0195 |
| CERVNOT01 | cervix, 35 F | 1 | 0.0194 |
| BRSTNOT04 | breast, 62 F | 2 | 0.0192 |
| MELANOM01 | melanocytes, M, NORM, WM | 2 | 0.0192 |

FIGURE 5B

| | | | |
|---|---|---|---|
| LUNGAST01 | lung, asthma, 17 M | 2 | 0.0189 |
| SYNOOAT01 | synovium, knee, osteoarthritis, 82 F | 1 | 0.0180 |
| MMLR2DT01 | macrophages (adher PBMNC), M/F, 48-hr MLR | 1 | 0.0178 |
| SYNORAT04 | synovium, wrist, rheumatoid, 62 F | 1 | 0.0174 |
| HNT2NOT01 | hNT2 cell line, teratocarcinoma, control | 1 | 0.0173 |
| UCMCL5T01 | mononuclear cells, treated IL-5 | 2 | 0.0168 |
| CONNNOT01 | fat, mesentary, 71 M | 1 | 0.0149 |
| BRSTTUT02 | breast tumor, 54 F, match to BRSTNOT03 | 1 | 0.0140 |
| BRAITUT01 | brain tumor, oligoastrocytoma, 50 F | 1 | 0.0134 |
| SINTFET03 | small intestine, fetal F | 1 | 0.0130 |
| KIDNNOT05 | kidney, neonatal F | 1 | 0.0106 |
| CORPNOT02 | brain, corpus callosum, Alzheimer's, 74 M | 1 | 0.0103 |
| BRSTTUT01 | breast tumor, 55 F, match to BRSTNOT02 | 1 | 0.0095 |
| LUNGFET03 | lung, fetal F | 1 | 0.0091 |
| BRAINOM01 | brain, infant F, NORM, WM | 1 | 0.0045 |

FIGURE 5C

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 235 amino acids
      (B) TYPE: amino acid
      (C) STRANDEDNESS: single
      (D) TOPOLOGY: linear (vii) IMMEDIATE SOURCE:
      (A) LIBRARY: lungast01
      (B) CLONE: 876242

(xi) SEQUENCE DESCRIPTION: SEQ ID NO:1:

```
Met Pro His Ala Phe Lys Pro Gly Asp Leu Val Phe Ala Lys Met Lys
1               5                   10                  15

Gly Tyr Pro His Trp Pro Ala Arg Ile Asp Asp Ile Ala Asp Gly Ala
            20                  25                  30

Val Lys Pro Pro Pro Asn Lys Tyr Pro Ile Phe Phe Phe Gly Thr His
        35                  40                  45

Glu Thr Ala Phe Leu Gly Pro Lys Asp Leu Phe Pro Tyr Glu Glu Ser
    50                  55                  60

Lys Glu Lys Phe Gly Lys Pro Asn Lys Arg Lys Gly Phe Ser Glu Gly
65                  70                  75                  80

Leu Trp Glu Ile Glu Asn Asn Pro Thr Val Lys Ala Ser Gly Tyr Gln
                85                  90                  95

Ser Ser Gln Lys Lys Ser Cys Val Glu Glu Pro Glu Pro Glu Pro Glu
            100                 105                 110

Ala Ala Glu Gly Asp Gly Asp Lys Lys Gly Asn Ala Glu Gly Ser Ser
        115                 120                 125

Asp Glu Glu Gly Lys Leu Val Ile Asp Glu Pro Ala Lys Glu Lys Asn
    130                 135                 140

Glu Lys Gly Ala Leu Lys Arg Arg Ala Gly Asp Leu Leu Glu Asp Ser
145                 150                 155                 160

Pro Lys Arg Pro Lys Glu Ala Glu Asn Pro Glu Gly Glu Glu Lys Glu
```

```
                  165                 170                 175
Ala Ala Thr Leu Glu Val Glu Arg Pro Leu Pro Met Glu Val Glu Lys
                180                 185                 190

Asn Ser Thr Pro Ser Glu Pro Gly Ser Gly Arg Gly Pro Pro Xaa Xaa
            195                 200                 205

Xaa Xaa Xaa Xaa Xaa Xaa Xaa Xaa Glu Glu Ala Thr Lys Glu Asp Ala
        210                 215                 220

Glu Ala Pro Gly Ile Lys Ser His Glu Ser Leu
225                 230                 235
```

(2) INFORMATION FOR SEQ ID NO:2:

(i) SEQUENCE CHARACTERISTICS:
        (A) LENGTH: 869 base pairs
        (B) TYPE: nucleic acid
        (C) STRANDEDNESS: single
        (D) TOPOLOGY: linear (vii) IMMEDIATE SOURCE:
        (A) LIBRARY: lungast01
        (B) CLONE: 876242

(xi) SEQUENCE DESCRIPTION: SEQ ID NO:2:

```
CCGCTGCAGC CGCTTTCTGC GGCCTGGGCC TCTCGCCGTC AGCATGCCAC ACGCCTTCAA    60
GCCCGGGGAC TTGGTGTTCG CTAAGATGAA GGGCTACCCT CACTGGCCTG CCAGGATCGA   120
CGACATCGCG GATGGCGCCG TGAAGCCCCC ACCCAACAAG TACCCCATCT TTTTCTTTGG   180
CACACACGAA ACAGCCTTCC TGGGCCCCAA AGACCTCTTC CCTTACGAGG AATCCAAGGA   240
GAAGTTTGGC AAGCCCAACA AGAGGAAAGG GTTCAGCGAG GGCTGTGGG AGATCGAGAA   300
CAACCCTACT GTCAAGGCTT CCGGCTATCA GTCCTCCCAG AAAAAGAGCT GTGTGGAAGA   360
GCCTGAACCA GAGCCCGAAG CTGCAGAGGG TGACGGTGAT AAGAAGGGGA ATGCAGAGGG   420
CAGCAGCGAC GAGGAAGGGA AGCTGGTCAT TGATGAGCCA GCCAAGGAGA GAACGAGAA   480
AGGAGCGTTG AAGAGGAGCA CAGGGGACTT GCTGGAGGAC TCTCCTAAAC GTCCCAAGGA   540
GGCAGAAAAC CCTGAAGGAG AGGAGAAGGA GGCAGCCACC TTGGAGGTTG AGAGGCCCCT   600
TCCTATGGAG GTGGAAAAGA ATAGCACCCC CTCTGAGCCC GGCTCTGGCC GGGGGCCTCC   660
CCNNNNNNNN NNNNNNNNNN NNNNNNNNNA GGAAGAGGCT ACCAAGGAAG ATGCTGAGGC   720
CCCAGGCATC AAGAGTCATG AGAGCCTGTA GCCACCAATG TTTCAAGAGG AGCCCCCACC   780
CTGTTCCTGC TGCTGTCTGG GTGCTACTGG GGAAACTGGC CATGGGCTGC AAACTGGGNA   840
CCCCTTTTCC ANCNCAANCT GNTNTTCTT                                     869
```

(2) INFORMATION FOR SEQ ID NO:3:

(i) SEQUENCE CHARACTERISTICS:
        (A) LENGTH: 240 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 598956

(xi) SEQUENCE DESCRIPTION: SEQ ID NO:3:

```
Met Ser Arg Ser Asn Arg Gln Lys Glu Tyr Lys Cys Gly Asp Leu Val
 1               5                  10                  15

Phe Ala Lys Met Lys Gly Tyr Pro His Trp Pro Ala Arg Ile Asp Glu
                20                  25                  30
```

```
Met Pro Glu Ala Ala Val Lys Ser Thr Ala Asn Lys Tyr Gln Val Phe
         35                  40                  45

Phe Phe Gly Thr His Glu Thr Ala Phe Leu Gly Pro Lys Asp Leu Phe
     50                  55                  60

Pro Tyr Glu Glu Ser Lys Glu Lys Phe Gly Lys Pro Asn Lys Arg Lys
 65                  70                  75                  80

Gly Phe Ser Glu Gly Leu Trp Glu Ile Glu Asn Asn Pro Thr Val Lys
                 85                  90                  95

Ala Ser Gly Tyr Gln Ser Ser Gln Lys Lys Ser Cys Val Glu Glu Pro
             100                 105                 110

Glu Pro Glu Pro Glu Ala Ala Glu Gly Asp Gly Asp Lys Lys Gly Asn
         115                 120                 125

Ala Glu Gly Ser Ser Asp Glu Glu Gly Lys Leu Val Ile Asp Glu Pro
     130                 135                 140

Ala Lys Glu Lys Asn Glu Lys Gly Ala Leu Lys Arg Arg Ala Gly Asp
145                 150                 155                 160

Leu Leu Glu Asp Ser Pro Lys Arg Pro Lys Glu Ala Glu Asn Pro Glu
                 165                 170                 175

Gly Glu Glu Lys Glu Ala Ala Thr Leu Glu Val Glu Arg Pro Leu Pro
             180                 185                 190

Met Glu Val Glu Lys Asn Ser Thr Pro Ser Glu Pro Gly Ser Gly Arg
         195                 200                 205

Gly Pro Pro Gln Glu Glu Glu Glu Glu Asp Glu Glu Glu Ala
     210                 215                 220

Thr Lys Glu Asp Ala Glu Ala Pro Gly Ile Arg Asp His Glu Ser Leu
225                 230                 235                 240
```

(2) INFORMATION FOR SEQ ID NO:4:

(i) SEQUENCE CHARACTERISTICS:
        (A) LENGTH: 2376 base pairs
        (B) TYPE: nucleic acid
        (C) STRANDEDNESS: single
        (D) TOPOLOGY: linear (vii) IMMEDIATE SOURCE:
        (A) LIBRARY: GenBank
        (B) CLONE: 598956

(xi) SEQUENCE DESCRIPTION: SEQ ID NO:4:

```
GAGGAGGAGT GGGGACCGGG CGGGGGGTGG AGGAAGAGGC CTCGCGCAGA GGAGGGAGCA     60

ATTGAATTTC AAACACAAAC AACTCGACGA GCGCGCACCC ACCGCGCCGG AGCCTTGCCC    120

CGATCCGCGC CCGCCCCGTC CGTGCGGCGC GCGGGCGGAG ACGCCGTGGC CGCGCCGGAG    180

CTCGGGCCGG GGGCCACCAT CGAGGCGGGG GCCGCGCGAG GGCCGGAGCG GAGCGGCGCC    240

GCCACCGCCG CACGCGCAAA CTTGGGCTCG CGCTTCCCGG CCCGGCGCGG AGCCCGGGGC    300

GCCCGGAGCC CCGCCATGTC GCGATCCAAC CGGCAGAAGG AGTACAAATG CGGGGACCTG    360

GTGTTCGCCA AGATGAAGGG CTACCCACAC TGGCCGGCCC GGATTGACGA GATGCCTGAG    420

GCTGCCGTGA AATCAACAGC CAACAAATAC CAAGTCTTTT TTTTCGGGAC CCACGAGACG    480

GCATTCCTGG GCCCCAAAGA CCTCTTCCCT TACGAGGAAT CCAAGGAGAA GTTTGGCAAG    540

CCCAACAAGA GGAAAGGGTT CAGCGAGGGG CTGTGGGAGA TCGAGAACAA CCCTACTGTC    600

AAGGCTTCCG GCTATCAGTC CTCCCAGAAA AAGAGCTGTG TGGAAGAGCC TGAACCAGAG    660

CCCGAAGCTG CAGAGGGTGA CGGTGATAAG AAGGGGAATG CAGAGGGCAG CAGCGACGAG    720

GAAGGGAAGC TGGTCATTGA TGAGCCAGCC AAGGAGAAGA ACGAGAAAGG AGCGTTGAAG    780
```

```
AGGAGAGCAG GGGACTTGCT GGAGGACTCT CCTAAACGTC CCAAGGAGGC AGAAAACCCT    840

GAAGGAGAGG AGAAGGAGGC AGCCACCTTG GAGGTTGAGA GGCCCCTTCC TATGGAGGTG    900

GAAAAGAATA GCACCCCCTC TGAGCCCGGC TCTGGCCGGG GGCCTCCCCA AGAGGAAGAA    960

GAAGAGGAGG ATGAAGAGGA AGAGGCTACC AAGGAAGATG CTGAGGCCCC AGGCATCAGA   1020

GATCATGAGA GCCTGTAGCC ACCAATGTTT CAAGAGGAGC CCCCACCCTG TTCCTGCTGC   1080

TGTCTGGGTG CTACTGGGGA AACTGGCCAT GGCCTGCAAA CTGGGAACCC CTTTCCCACC   1140

CCAACCTGCT CTCCTCTTCT ACTCACTTTT CCCACTCCAA GCCCAGCCCA TGGAGATTGA   1200

CCTGGATGGG GCAGGCCACC TGGCTCTCAC CTCTAGGTCC CCATACTCCT ATGATCTGAG   1260

TCAGAGCCAT GTCTTCTCCC TGGAATGAGT TGAGGCCACT GTGTTCCTTC CGCTTGGAGC   1320

TATTTTCCAG GCTTCTGCTG GGGCCTGGGA CAACTGCTCC CACCTCCTGA CACCCTTCTC   1380

CCACTCTCCT AGGCATTCTG GACCTCTGGG TTGGGATCAG GGTAGGAAT GGAAGGATGG   1440

AGCATCAACA GCAGGGTGGG CTTGTGGGGC CTGGGAGGGG CAATCCTCAA ATGCGGGGTG   1500

GGGGCAGCAC AGGAGGGCGG CCTCCTTCTG AGCTCCTGTC CCCTGCTACA CCTATTATCC   1560

CAGCTGCCTA GATTCAGGGA AAGTGGGACA GCTTGTAGGG GAGGGCTCC TTTCCATAAA    1620

TCCTTGATGA TTGACAACAC CCATTTTTCC TTTTGCCGAC CCCAAGAGTT TTGGGAGTTG   1680

TAGTTAATCA TCAAGAGAAT TTGGGGCTTC CAAGTTGTTC GGGCAAGGA CCTGAGACCT    1740

GAAGGGTTGA CTTTACCCAT TTGGGTGGGA GTGTTGAGCA TCTGTCCCCC TTTAGATCTC   1800

TGAAGCCACA AATAGGATGC TTGGGAAGAC TCCTAGCTGT CCTTTTTCCT CTCCACACAG   1860

TGCTCAAGGC CAGCTTATAG TCATATATAT CACCCAGACA TAAAGGAAAA GACACATTTT   1920

TTAGGAAATG TTTTTAATAA AAGAAAATTA CAAAAAAAAA TTTTAAAGAC CCCTAACCCT   1980

TTGTGTGCTC TCCATTCTGC TCCTTCCCCA TCGTTGCCCC CATTTCTGAG GTGCACTGGG   2040

AGGCTCCCCT TCTATTTGGG GCTTGATGAC TTTCTTTTTG TAGCTGGGGC TTTGATGTTC   2100

CTTCCAGTGT CATTTCTCAT CCACATACCC TGACCTGGCC CCCTCAGTGT TGTCACCAGA   2160

TCTGATTTGT AACCCACTGA GAGGACAGAG AGAAATAAGT GCCCTCTCCC ACCCTCTTCC   2220

TACTGGTCTC TCTATGCCTC TCTACAGTCT CGTCTCTTTT ACCCTGGCCC CTCTCCCTTG   2280

GGCTCTGATG AAAAATTGCT GACTGTAGCT TTGGAAGTTT AGCTCTGAGA ACCGTAGATG   2340

ATTTCAGTTC TAGGAAAATA AAACCCGTTG ATTACT                             2376

(2) INFORMATION FOR SEQ ID NO:5:

(i) SEQUENCE CHARACTERISTICS:
        (A) LENGTH: 237 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 945419

(xi) SEQUENCE DESCRIPTION: SEQ ID NO:5:

Met Ser Arg Ser Asn Arg Gln Lys Glu Tyr Lys Cys Gly Asp Leu Val
 1               5                  10                  15

Phe Ala Lys Met Lys Gly Tyr Pro His Trp Pro Ala Arg Ile Asp Glu
                20                  25                  30

Met Pro Glu Ala Ala Val Lys Ser Thr Ala Asn Lys Tyr Gln Val Phe
            35                  40                  45

Phe Phe Gly Thr His Glu Thr Ala Phe Leu Gly Pro Lys Asp Leu Phe
        50                  55                  60
```

```
Pro Tyr Glu Glu Ser Lys Glu Lys Phe Gly Lys Pro Asn Lys Arg Lys
65              70              75              80

Gly Phe Ser Glu Gly Leu Trp Glu Ile Glu Asn Asn Pro Thr Val Lys
            85              90              95

Ala Ser Gly Tyr Gln Ser Ser Gln Lys Lys Ser Cys Ala Ala Glu Pro
            100             105             110

Glu Val Glu Pro Glu Ala His Glu Gly Asp Gly Asp Lys Lys Gly Ser
        115             120             125

Ala Glu Gly Ser Ser Asp Glu Glu Gly Lys Leu Val Ile Asp Glu Pro
    130             135             140

Ala Lys Glu Lys Asn Glu Lys Gly Thr Leu Lys Arg Arg Ala Gly Asp
145             150             155             160

Val Leu Glu Asp Ser Pro Lys Arg Pro Lys Glu Ser Gly Asp His Glu
            165             170             175

Glu Glu Asp Lys Glu Ile Ala Ala Leu Glu Gly Glu Arg His Leu Pro
            180             185             190

Val Glu Val Glu Lys Asn Ser Thr Pro Ser Glu Pro Asp Ser Gly Gln
        195             200             205

Gly Pro Pro Ala Glu Glu Glu Gly Glu Glu Glu Ala Ala Lys Glu
    210             215             220

Glu Ala Glu Ala Pro Gly Val Arg Asp His Glu Ser Leu
225             230             235
```

DNA ENCODING LUNG GROWTH FACTOR VARIANT

FIELD OF THE INVENTION

This invention relates to nucleic acid and amino acid sequences of a lung growth factor variant and to the use of these sequences in the diagnosis, prevention, and treatment of various infections, pregnancy, autoimmune disorders, vascular diseases, and cancers.

BACKGROUND OF THE INVENTION

Hepatoma derived growth factors (HDGF) have been cloned from man and mouse. When they bind to specific membrane receptors, they trigger intracellular signaling cascades. Some of these signaling events control the activities of transcription factors. The unregulated activity of transcription factors which govern cell proliferation may result in the growth and development of cancerous cells or in the release and differentiation of excess leukocytes.

Nakamura et al. (1994; J. Biol. Chem. 269:25143–49) described the human HDGF molecule as a monomeric, cytoplasmic peptide of 240 amino acids and approximately 25 kD which lacks a signal sequence and binds heparin. Northern analysis revealed that HDGF is expressed in several tumor derived cell lines and in heart, brain, placenta, lung, liver, skeletal muscle, kidney and pancreas. Based on its homology to high mobility group proteins (HMGs), location in the cytoplasm, and association with cellular proliferation in both normal and tumor cells, Nakamura et al (supra) predict that HDGF is a transcription factor which shows growth stimulating activity.

Baxevanis and Landsman (1995; Nucleic Acids Res 23:1604–13) aligned 121 HMG basic domains and reported that they fall into two groups, the HMG1/2 proteins with DNA binding ability and non-canonical HMGs, some of which are known to function as transcription factors. HMG1/2 proteins bind and alter the structure of DNA, making the molecule more amenable to the enzymes which carry out transcription. Support for this role comes from the fact that the half life of HMG1/2 proteins directly parallels the S phase of the cell cycle (Morton, R. L. et al. (1996) Biochem. Biophys Res Commun. 222:268–373). Other studies have shown that some HMGs possess a calmodulin binding domain (Harley, V. R. et al. (1996) FEBS Lett 391:24–28) and others associate with either hormone receptors as they bind DNA (Onate, S. A. et al. (1994) Mol Cell Biol 14:3376–91) or T-cell receptors as they regulate lymphocyte gene expression. These proteins enhance gene expression in the cells and tissues in which they are present.

HMGs have also been studied to determine their role in transforming fibroblasts and hematopoietic cells, in Burkitt's lymphoma (Morton, et al. supra), and in gastrointestinal carcinomas.

The discovery of polynucleotides encoding a lung growth factor variant, and the variant itself, provides a means to investigate cell proliferation under normal and disease conditions. Such cytokines or growth factor-like molecules related to hepatoma growth factor satisfy a need in the art by providing new diagnostic or therapeutic compositions useful in diagnosing and treating infections; autoimmune disorders, vascular diseases and cancers.

SUMMARY OF THE INVENTION

The present invention features a novel lung growth factor variant hereinafter designated LGFV and characterized as having 75% identity over the first 196 nucleotides and 90% identity overall to hepatoma derived growth factor.

Accordingly, the invention features a substantially purified LGFV having the amino acid sequence shown in SEQ ID NO:1.

One aspect of the invention features isolated and substantially purified polynucleotides that encode LGFV. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode LGFV. The present invention also features antibodies which bind specifically to LGFV, and pharmaceutical compositions comprising substantially purified LGFV. The invention also features the use of agonists and antagonists of LGFV.

BRIEF DESCRIPTION OF THE FIGURES

FIGS. 1A and 1B show the amino acid sequence (SEQ ID NO:1) and nucleic acid sequence (SEQ ID NO:2) of LGFV. The alignment was produced using MACDNASIS PRO™ software (Hitachi Software Engineering Co., Ltd., San Bruno, Calif.).

FIG. 2 shows the amino acid sequence alignments among LGFV (SEQ ID NO:1), and hepatoma growth factors from man and mouse (GI 598956; SEQ ID NO:3 and GI 945419; Seq ID NO:5, respectively). The alignment was produced using the multisequence alignment program of DNASTAR™ software (DNASTAR Inc, Madison Wis.).

FIGS. 3A and 3B show the nucleotide sequence alignments among LGFV (SEQ ID NO:2), and human hepatoma growth factor (GI 598956; SEQ ID NO:4).

FIGS. 5A, 5B, and 5C show the northern analysis of LGFV produced using the LIFESEQ® database (Incyte Pharmaceuticals Inc., Palo Alto, Calif.).

DESCRIPTION OF THE INVENTION

Figure 4A:
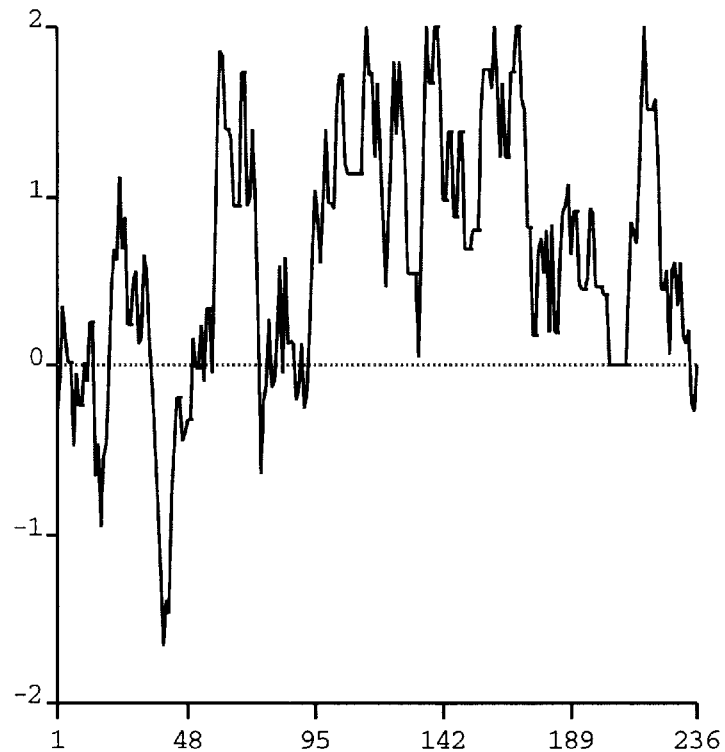
FIGS. 4A and 4B show the hydrophobicity plots (MACDNASIS PRO software) for LGFV (SEQ ID NO:1) and hepatoma growth factor (GI 598956; SEQ ID NO:3); the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

LGFV, as used herein, refers to the amino acid sequences of substantially purified LGFV obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of LGFV, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic LGFV, or any oligopeptide thereof, to induce a specific immune response in appropriate animals or cells and to bind with specific antibodies.

The term "agonist", as used herein, refers to a molecule which, when bound to LGFV, causes a change in LGFV which modulates the activity of LGFV. Agonists may include proteins, nucleic acids, carbohydrates, or any other molecules which bind to LGFV.

The terms "antagonist" or "inhibitor", as used herein, refer to a molecule which, when bound to LGFV, blocks or modulates the biological or immunological activity of LGFV. Antagonists and inhibitors may include proteins, nucleic acids, carbohydrates, or any other molecules which bind to LGFV.

The term "modulate", as used herein, refers to a change or an alteration in the biological activity of LGFV. Modulation may be an increase or a decrease in protein activity, a change in binding characteristics, or any other change in the biological, functional or immunological properties of LGFV.

The term "mimetic", as used herein, refers to a molecule, the structure of which is developed from knowledge of the structure of LGFV or portions thereof and, as such, is able to effect some or all of the actions of cytokine-like molecules.

The term "derivative", as used herein, refers to the chemical modification of a nucleic acid encoding LGFV or the encoded LGFV. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual,* Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_o t$ or $R_o t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human LGFV and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding LGFV or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding LGFV in a sample and thereby correlates with expression of the transcript from the polynucleotide encoding the protein.

"Alterations" in the polynucleotide of SEQ ID NO:2, as used herein, comprise any alteration in the sequence of polynucleotides encoding LGFV including deletions, insertions, and point mutations that may be detected using hybridization assays. Included within this definition is the detection of alterations to the genomic DNA sequence which encodes LGFV (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding LGFV (e.g., using fluorescent in situ hybridization [FISH] to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind LGFV polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a novel lung growth factor variant, (LGFV), the polynucleotides encoding LGFV, and the use of these sequences in the diagnosis, prevention, and treatment of various infections; pregnancy, autoimmune disorders, vascular diseases, and cancers.

Nucleic acids encoding the human LGFV of the present invention were first identified in Incyte Clone 876242 from the asthmatic lung cDNA library (LUNGAST01) through a computer-generated search for amino acid sequence alignments. A consensus sequence, SEQ ID NO:2, was derived from the following overlapping and/or extended nucleic acid sequences: Incyte Clones 157389 and 157561 (THP1PLB02), 180392 (SINTNOT13), 269860 (HNT2NOT01), 667981 (SCORNOT01), 876242 (LUNGAST01), 917859 (BRSTNOT04), 938690 (CERVNOT01), 1336691 (COLNNOT11), and 1344641 (PROSNOT11).

Figure 2:
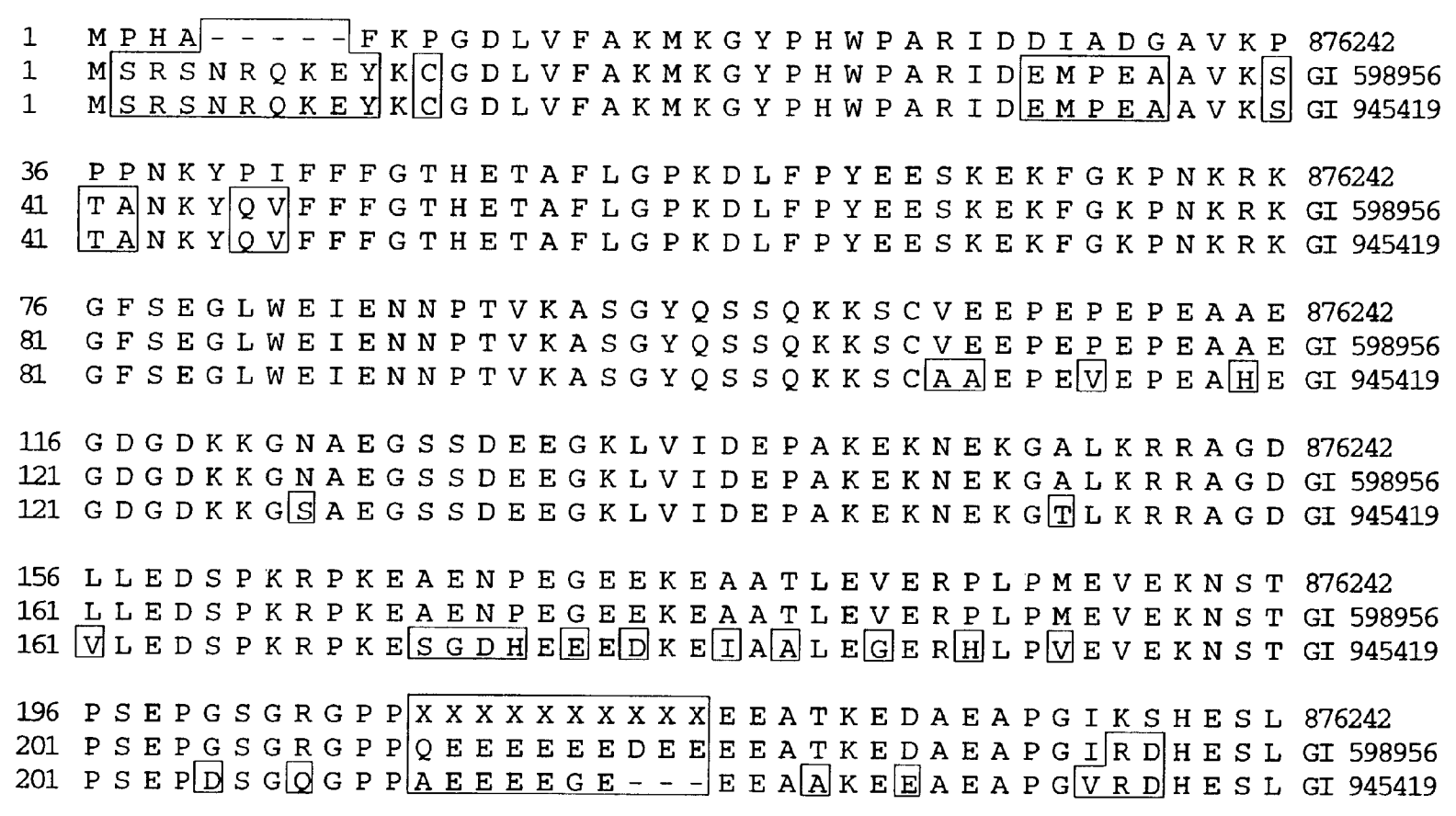
Figure 4B:
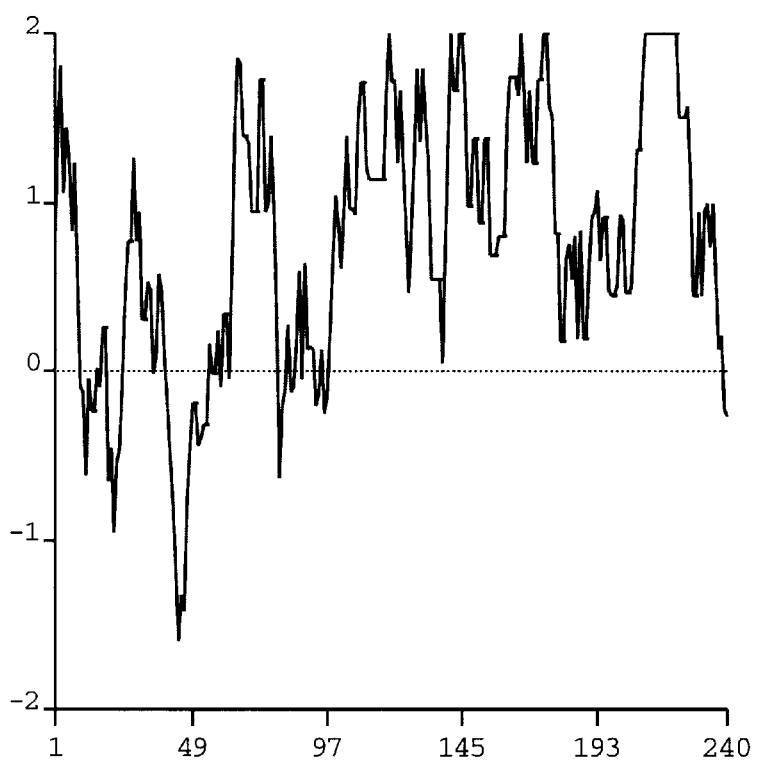

In one embodiment, the invention encompasses a polypeptide comprising the amino acid sequence of SEQ ID NO:1, as shown in FIG. 1A and 1B. LGFV is 235 amino acids in length and lacks any potential N-linked glycosylation sites. LGFV has chemical and structural homology with hepatoma derived growth factor (GI 598956; SEQ ID NO:3). In particular, LGFV and hepatoma derived growth factor share 75% identity over the first 196 nucleotides which encode the proteins (FIGS. 3A and 3B), and 90% identity over the entire length of the nucleotide and amino acid sequences (FIGS. 2, 3A and 3B). As illustrated by FIGS. 4A and 4B, LGFV and lung growth factor have rather similar hydrophobicity plots.

Northern analysis (FIGS. 5A, 5B, and 5C) shows the expression of this sequence in 115 libraries, at least 51% of which are immortalized or cancerous and at least 28% of which involve immune response. Of particular note is the expression of LGFV in cancers of the brain (~4%), breast (~6%) gastrointestinal tract (~7%), lungs (~10%), pancreas (~3%), male reproductive system (~9%), urinary tract (~3%), thyroid (~2%) and female reproductive system (~3%) and in leukocytes including granulocytes, lymphocytes, and macrophages. In many of these tissues, particularly those of the brain, breast, thyroid and those of the female and male reproductive systems, cell proliferation may involve association between LGFV and steroid hormone receptors.

The invention also encompasses LGFV variants. A preferred LGFV variant is one having at least 90% amino acid sequence similarity to the LGFV amino acid sequence (SEQ ID NO:1). A most preferred LGFV variant is one having at least 95% amino acid sequence similarity to SEQ ID NO:1.

The invention also encompasses polynucleotides which encode LGFV. Accordingly, any nucleic acid sequence which encodes the amino acid sequence of LGFV can be used to generate recombinant molecules which express LGFV. In a particular embodiment, the invention encompasses the polynucleotide comprising the nucleic acid sequence of SEQ ID NO:2 as shown in FIG. 1.

It will be appreciated by those skilled in the art that as a result of the degeneracy of the genetic code, a multitude of nucleotide sequences encoding LGFV, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring LGFV, and all such variations are to be considered as being specifically disclosed.

Although nucleotide sequences which encode LGFV and its variants are preferably capable of hybridizing to the nucleotide sequence of the naturally occurring LGFV under appropriately selected conditions of stringency, it may be advantageous to produce nucleotide sequences encoding LGFV or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding LGFV and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode LGFV and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding LGFV or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding LGFV which are encompassed by the invention include deletions, insertions, or substitutions of different nucleotides resulting in a polynucleotide that encodes the same or a functionally equivalent LGFV. The encoded protein may also contain deletions, insertions, or substitutions of amino acid residues which produce a silent change and result in a functionally equivalent LGFV. Deliberate amino acid substitutions may be made on the basis of similarity in polarity, charge, solubility, hydrophobicity, hydrophilicity, and/or the amphipathic nature of the residues as long as the biological activity of LGFV is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding LGFV. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding LGFV may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENETYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode LGFV, or fusion proteins or functional equivalents thereof, may be used in recombinant DNA molecules to direct expression of LGFV in appropriate host cells. Due to the inherent degeneracy of the genetic code, other DNA sequences which encode substantially the same or a functionally equivalent amino acid sequence may be produced and these sequences may be used to clone and express LGFV.

As will be understood by those of skill in the art, it may be advantageous to produce LGFV-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter LGFV encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding LGFV may be ligated to a heterologous sequence to encode a fusion protein. For example, to screen peptide libraries for inhibitors of LGFV activity, it may be useful to encode a chimeric LGFV protein that can be recognized by a commercially available antibody. A fusion protein may also be engineered to contain a cleavage site located between the LGFV encoding sequence and the heterologous protein sequence, so that LGFV may be cleaved and purified away from the heterologous moiety.

In another embodiment, sequences encoding LGFV may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of LGFV, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W H Freeman and Co., New York, N.Y.). The composition of the synthetic peptides may be confirmed by amino acid analysis or sequencing (e.g., the Edman degradation procedure; Creighton, supra). Additionally, the amino acid sequence of LGFV, or any part thereof, may be altered during direct synthesis and/or combined using chemical methods with sequences from other proteins, or any part thereof, to produce a variant polypeptide.

In order to express a biologically active LGFV, the nucleotide sequences encoding LGFV or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding LGFV and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding LGFV. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, Calif.) or PSPORTI plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding LGFV, vectors based on SV40 or EBV may be used with an appropriate selectable marker.

In bacterial systems, a number of expression vectors may be selected depending upon the use intended for LGFV. For example, when large quantities of LGFV are needed for the induction of antibodies, vectors which direct high level expression of fusion proteins that are readily purified may be used. Such vectors include, but are not limited to, the multifunctional *E. coli* cloning and expression vectors such as BLUESCRIPT® (Stratagene), in which the sequence encoding LGFV may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding LGFV may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express LGFV. For example, in one such system, *Autographa californica* nuclear polyhedrosis virus (AcNPV) is used as a vector to express foreign genes in *Spodoptera frugiperda* cells or in Trichoplusia larvae. The sequences encoding LGFV may be cloned into a non-essential region of the virus, such as the polyhedrin gene, and placed under control of the polyhedrin promoter. Successful insertion of LGFV will render the polyhedrin gene inactive and produce recombinant virus lacking coat protein. The recombinant viruses may then be used to infect, for example, *S. frugiperda* cells or Trichoplusia larvae in which LGFV may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding LGFV may be ligated into an adenovirus transcription/translation complex consisting of the late promoter and tripartite leader sequence. Insertion in a non-essential E1 or E3 region of the viral genome may be used to obtain a viable virus which is capable of expressing LGFV in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding LGFV. Such signals include the ATG initiation codon and adjacent sequences. In cases where sequences encoding LGFV, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express LGFV may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding LGFV is inserted within a marker gene sequence, recombinant cells containing sequences encoding LGFV can be identified by the absence of marker gene function. Alternatively, a marker gene can be placed in tandem with a sequence encoding LGFV under the control of a single promoter. Expression of the marker gene in response to induction or selection usually indicates expression of the tandem gene as well.

Alternatively, host cells which contain the nucleic acid sequence encoding LGFV and express LGFV may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding LGFV can be detected by DNA-DNA or DNA-RNA hybridization or amplification using probes or portions or fragments of polynucleotides encoding LGFV. Nucleic acid amplification based assays involve the use of oligonucleotides or oligomers based on the sequences encoding LGFV to detect transformants containing DNA or RNA encoding LGFV. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of LGFV, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on LGFV is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding LGFV include oligolabeling, nick translation, end-labeling or PCR amplification using a labeled nucleotide. Alternatively, the sequences encoding LGFV, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding LGFV may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode LGFV may be designed to contain signal sequences which direct secretion of LGFV through a prokaryotic or eukaryotic cell membrane. Other recombinant constructions may be used to join sequences encoding LGFV to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and LGFV may be used to facilitate purification. One such expression vector provides for expression of a fusion protein containing LGFV and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying LGFV from the fusion protein. A discussion of vectors which contain fusion proteins is provided in Kroll, D. J. et al. (1993; DNA Cell Biol. 12:441–453).

In addition to recombinant production, fragments of LGFV may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of LGFV may be chemically synthesized separately and combined using chemical methods to produce the full length molecule

THERAPEUTICS

Based on the chemical and structural homology among LGFV (SEQ ID NO:1) and HDGFs from man (SEQ ID NO:3) and mouse (SEQ ID NO:4), the expression of LGFV in brain, breast, female reproductive system, fetal tissues, gastrointestinal tract, lungs, pancreas, male reproductive system, thyroid and urinary tract, in leukocytes including granulocytes, lymphocytes, and macrophages, and in many immortalized cell lines, LGFV appears to play a role in growth and development as well as in infections, pregnancy, autoimmune diseases, vascular conditions and cancers.

Therefore, in one embodiment, LGFV or a fragment or derivative thereof may be used to treat cells in vivo or ex vivo for the purposes of tissue or organ regeneration. This embodiment would be of particular benefit in the proliferation and differentiation of bone marrow, nerve, pancreatic or renal cells.

In another embodiment, a vector capable of expressing LGFV, or a fragment or derivative thereof, may also be administered to a cell culture or a subject for ex vivo or in vivo therapy as previously above.

In one aspect, antibodies which are specific for LGFV may be used directly as an antagonist or indirectly as a targeting or delivery mechanism for bringing a pharmaceutical agent to cells or tissues which express excessive amounts of LGFV.

In one embodiment, antagonists or inhibitors of LGFV may be administered to a subject to prevent cancerous cell proliferation and/or tissue damage due to excessive leukocytes produced during autoimmune or immunological responses. Such cancers may include, but are not limited to, leukemia, lymphomas or carcinomas. Excessive immunological response may be that which is attributed to, but is not limited to, viral (AIDS), bacterial (pulmonary pneumonia, hepatitis or septic shock), fungal (histoplasmosis, leprosy) or helminthic/parasitic infections; allergies or asthma; arteriosclerosis, atherogenesis or collagen vascular diseases; and autoimmune diseases such as hemolytic anemia, biliary cirrhosis, Crohn's disease, diabetes mellitus, lupus erythematosus, multiple sclerosis, myasthenia gravis, or rheumatoid arthritis.

In another aspect, inhibitors of LGFV can be administered in a suitable formulation to prevent spermatogenesis in mammalian reproductive tissues, thereby effecting birth control.

In another embodiment, a vector expressing antisense of the polynucleotide encoding LGFV may be administered to a subject to prevent growth and development of cancerous cells or to modulate the progression of the autoimmune diseases listed above or the proliferation of leukocytes which cause tissue destruction and are associated with infections or immunological response as described above.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of LGFV may be produced using methods which are generally known in the art. In particular, purified LGFV may be used to produce antibodies or to screen libraries of pharmaceutical agents to identify those which specifically bind LGFV.

Antibodies which are specific for LGFV may be used directly as an antagonist, or indirectly as a targeting or delivery mechanism for bringing a pharmaceutical agent to cells or tissue which express LGFV. The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with LGFV or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to LGFV have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of LGFV amino acids may be fused with those of another protein such as keyhole limpet hemocyanin and antibody produced against the chimeric molecule.

Monoclonal antibodies to LGFV may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce LGFV-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for LGFV may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between LGFV and its specific antibody. A two-site, monoclonal-based immunoassay utilizing monoclonal antibodies reactive to two non-interfering LGFV epitopes is preferred, but a competitive binding assay may also be employed (Maddox, supra).

In another embodiment of the invention, the polynucleotides encoding LGFV, or any fragment thereof, or antisense molecules, may be used for therapeutic purposes. In one aspect, antisense to the polynucleotide encoding LGFV may be used in situations in which it would be desirable to block the transcription of the mRNA. In particular, cells may be transformed with sequences complementary to polynucleotides encoding LGFV. Thus, antisense molecules may be used to modulate LGFV activity, or to achieve regulation of gene function. Such technology is now well known in the art, and sense or antisense oligomers or larger fragments, can be designed from various locations along the coding or control regions of sequences encoding LGFV.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding LGFV. These techniques are described both in Sambrook et al. (supra) and in Ausubel et al. (supra).

Genes encoding LGFV can be turned off by transforming a cell or tissue with expression vectors which express high levels of a polynucleotide or fragment thereof which encodes LGFV. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding LGFV, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding LGFV.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding LGFV. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of LGFV, antibodies to LGFV, mimetics, agonists, antagonists, or inhibitors of LGFV. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of LGFV, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example LGFV or fragments thereof, antibodies of LGFV, agonists, antagonists or inhibitors of LGFV, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind LGFV may be used for the diagnosis of conditions or diseases characterized by expression of LGFV, or in assays to monitor patients being treated with LGFV, agonists, antagonists or inhibitors. The antibodies useful for diagnostic purposes may be prepared in the same manner as those described above for therapeutics. Diagnostic assays for LGFV include methods which utilize the antibody and a label to detect LGFV in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring LGFV are known in the art and provide a basis for diagnosing altered or abnormal levels of LGFV expression. Normal or standard values for LGFV expression are established by combining body fluids or cell extracts taken from normal mammalian subjects, preferably human, with antibody to LGFV under conditions suitable for complex formation The amount of standard complex formation may be quantified by various methods, but preferably by photometric, means. Quantities of LGFV expressed in subject, control and disease, samples from biopsied tissues are compared with the standard values. Deviation between standard and subject values establishes the parameters for diagnosing disease.

In another embodiment of the invention, the polynucleotides encoding LGFV may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of LGFV may be correlated with disease. The diagnostic assay may be used to distinguish between absence, presence, and excess expression of LGFV, and to monitor regulation of LGFV levels during therapeutic intervention.

In one aspect, hybridization with PCR probes which are capable of detecting polynucleotide sequences, including genomic sequences, encoding LGFV or closely related molecules, may be used to identify nucleic acid sequences which encode LGFV. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding LGFV, alleles, or related sequences.

Probes may also be used for the detection of related sequences, and should preferably contain at least 50% of the nucleotides from any of the LGFV encoding sequences. The hybridization probes of the subject invention may be DNA or RNA and derived from the nucleotide sequence of SEQ ID NO:2 or from genomic sequence including promoter, enhancer elements, and introns of the naturally occurring LGFV.

Means for producing specific hybridization probes for DNAs encoding LGFV include the cloning of nucleic acid sequences encoding LGFV or LGFV derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}P$ or $^{35}S$, or enzymatic labels, such as alkaline phosphatase coupled to the probe via avidin/biotin coupling systems, and the like.

Polynucleotide sequences encoding LGFV may be used for the diagnosis of conditions or diseases which are associated with excessive expression of LGFV. Examples include infections, pregnancy, autoimmune diseases, vascular conditions and cancers. These specifically include, but are not limited to, conditions with similar biochemical, mitogenic, or immunological properties such as viral (AIDS), bacterial (pulmonary pneumonia, hepatitis or septic shock), fungal (histoplasmosis, leprosy) or helminthic/parasitic infections; allergies or asthma; mechanical injury through exposure (to asbestos, coal dust, etc) or trauma; arteriosclerosis, atherogenesis or collagen vascular diseases; hereditary diseases such as autoimmune hemolytic anemia, biliary cirrhosis, Crohn's disease, diabetes mellitus, lupus erythematosus, multiple sclerosis, myasthenia gravis, or rheumatoid arthritis; spermatogenesis, and leukemia, lymphomas or carcinomas The polynucleotide sequences encoding LGFV may be used in Southern or northern analysis, dot blot, or other membrane-based technologies; in PCR technologies; or in dip stick, pin, ELISA or chip assays utilizing fluids or tissues from patient biopsies to detect altered LGFV expression. Such qualitative or quantitative methods are well known in the art.

In a particular aspect, the nucleotide sequences encoding LGFV may be useful in assays that detect activation or induction of various cancers, particularly those mentioned above. The nucleotide sequences encoding LGFV may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding LGFV in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of LGFV, a normal or standard profile for expression is established. This may be accomplished by combining body fluids or cell extracts taken from normal subjects, either animal or human, with a sequence, or a fragment thereof, which encodes LGFV, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding LGFV may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of LGFV include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode LGFV may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding LGFV on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, LGFV, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between LGFV and the agent being tested, may be measured.

Another technique for drug screening which may be used provides for high throughput screening of compounds having suitable binding affinity to the protein of interest as described in published PCT application WO84/03564. In this method, as applied to LGFV large numbers of different small test compounds are synthesized on a solid substrate, such as plastic pins or some other surface. The test compounds are reacted with LGFV, or fragments thereof, and washed. Bound LGFV is then detected by methods well known in the art. Purified LGFV can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding LGFV specifically compete with a test compound for binding LGFV. In this manner, the antibodies can be used to detect the presence of any peptide which shares one or more antigenic determinants with LGFV.

In additional embodiments, the nucleotide sequences which encode LGFV may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I LUNGAST01 cDNA Library Construction

The LUNGAST01 cDNA library was constructed from cryopreserved lung purchased from Clonetics (San Diego Calif.; catalog #CC-2501, tissue lot no. 2199;). The tissue donor was a 30 year old Afro-American female who underwent elective breast reduction surgery. At the time of surgery, the donor was taking ferrous sulfate in preparation for the surgery, and a routine blood test was unremarkable except for a slight elevation of serum alanine transferase. The patient reported tobacco use, but no associated symptoms and no prior surgery.

The cells were lysed using a Brinkmann Homogenizer Polytron PT-3000 (Brinkmann Instruments, Westbury N.J.) in guanidinium isothiocyanate. The lysate was centrifuged over a 5.7 M CsCl cushion using a Beckman SW28 rotor in a Beckman L8-70M Ultracentrifuge (Beckman Instruments) for 18 hours at 25,000 rpm at ambient temperature. The RNA was extracted with phenol chloroform pH 8.0, precipitated using 0.3 M sodium acetate and 2.5 volumes of ethanol, resuspended in RNAse-free water and DNase treated at 37° C. The RNA was reextracted with phenol chloroform and precipitated using sodium acetate and ethanol as before. The mRNA was then isolated using the Qiagen OLIGOTEX kit (QIAGEN Inc; Chatsworth Calif.) and used to construct the cDNA library.

The mRNA was handled according to the recommended protocols in the SUPERSCRIPT™ Plasmid System for cDNA Synthesis and Plasmid Cloning (Cat. #18248-013; Gibco/BRL). cDNAs were fractionated on a Sepharose CL4B column (Cat. #275105; Pharmacia), and those cDNAs exceeding 400 bp were ligated into PSPORTI™. The plasmid PSPORTI™ was subsequently transformed into DH5a™ competent cells (Cat. #18258-012; Gibco/BRL).

II Isolation and Sequencing of cDNA Clones

Plasmid DNA was released from the cells and purified using the REAL Prep 96 Plasmid kit (Catalog #26173; Qiagen, Inc). This kit enables the simultaneous purification of 96 samples in a 96-well format using multi-channel reagent dispensers. The recommended protocol was employed except for the following changes: 1) the bacteria were cultured in 1 ml of sterile Terrific Broth (Catalog #22711, LIFE TECHNOLOGIES™, Gaithersburg, Md.) with carbenicillin at 25 mg/L and glycerol at 0.4%; 2) the cultures were incubated for 19 hours and then lysed with 0.3 ml of lysis buffer; 3) following isopropanol precipitation, the plasmid DNA pellet was resuspended in 0.1 ml of distilled water. After the last step in the protocol, samples were transferred to a Beckman 96-well block for storage at 4° C.

The cDNAs were sequenced by the method of Sanger F and AR Coulson (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems; and the reading frame was determined.

III Homology Searching of cDNA Clones and their Deduced Proteins

The nucleotide sequences (or amino acid sequences deduced from them) were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul (1993) supra, Altschul (1990) supra).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith RF and TF Smith (1992 Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin and Altschul (supra) and incorporated herein by reference, searches for matches between a query sequence and a database sequence, evaluates the statistical significance of any matches found, and reports only those matches which satisfy the user-selected threshold of significance. In this application, threshold was set at $10^{-25}$ for nucleotides and $10^{-14}$ for peptides. Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ® database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding LGFV occurs. Abundance and percent abundance are also reported. Abundance directly reflects the number of times a particular transcript is represented in a cDNA library, and percent abundance is abundance divided by the total number of sequences examined in the cDNA library.

V Extension of LGFV-Encoding Polynucleotides to Full Length or to Recover Regulatory Sequences Full length LGFV-encoding nucleic acid sequence (SEQ ID NO:2) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK™ (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1µl T4-DNA ligase (15 units) and 1µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 μl of liquid LB/2× Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

Step 1 94° C. for 60 sec

Step 2 94° C. for 20 sec

Step 3 55° C. for 30 sec

Step 4 72° C. for 90 sec

Step 5 Repeat steps 2–4 for an additional 29 cycles

Step 6 72° C. for 180 sec

Step 7 4° C. (and holding)

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 μCi of [γ-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the LGFV-encoding sequence, or any part thereof, is used to inhibit in vivo or in vitro expression of naturally occurring LGFV. Although use of antisense oligonucleotides, comprising about 20 base-pairs, is specifically described, essentially the same procedure is used with larger cDNA fragments. An oligonucleotide based on the coding sequences of LGFV, as shown in FIGS. 1A and 1B, is used to inhibit expression of naturally occurring LGFV. The complementary oligonucleotide is designed from the most unique 5' sequence as shown in FIGS. 1A and 1B and used either to inhibit transcription by preventing promoter binding to the upstream nontranslated sequence or translation of an LGFV-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A and 1B.

VIII Expression of LGFV

Expression of LGFV is accomplished by subcloning the cDNAs into appropriate vectors and transforming the vectors into host cells. In this case, the cloning vector, pSport, previously used for the generation of the cDNA library is used to express LGFV in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of LGFV into the bacterial growth media which can be used directly in the following assay for activity.

IX Demonstration of LGFV Activity

Purified LGFV, or a vector for expressing the protein, can be added to a mammalian cell culture using electroporation, liposome technology or other methods well known in the art. The presence of this cell cycle enhancer will increase the number of cell going through the cell cycle. Increased cell division/proliferation can be monitored in liquid culture by noting increases in cell number/ml of culture media using densitometry. Unstimulated vs stimulated cells will have different doubling times. Alternatively the mitotic index of control and treated subcultures may be compared using phase contrast microscopy.

X Production of LGFV Specific Antibodies

LGFV that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated goat anti-rabbit IgG.

XI Purification of Naturally Occurring LGFV Using Specific Antibodies

Naturally occurring or recombinant LGFV is substantially purified by immunoaffinity chromatography using antibodies specific for LGFV. An immunoaffinity column is constructed by covalently coupling LGFV antibody to an activated chromatographic resin, such as CnBr-activated Sepharose (Pharmacia & Upjohn). After the coupling, the resin is blocked and washed according to the manufacturer's instructions.

Media containing LGFV is passed over the immunoaffinity column, and the column is washed under conditions that allow the preferential absorbance of LGFV (e.g., high ionic strength buffers in the presence of detergent). The column is eluted under conditions that disrupt antibody/LGFV binding (eg, a buffer of pH 2–3 or a high concentration of a chaotrope, such as urea or thiocyanate ion), and LGFV is collected.

XII Identification of Molecules Which Interact with LGFV

LGFV or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled LGFV, washed and any wells with labeled LGFV complex are assayed. Data obtained using different concentrations of LGFV are used to calculate values for the number, affinity, and association of LGFV with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified polynucleotide sequence encoding the lung growth factor variant (LGVF) having the amino acid sequence of SEQ ID NO:1.
2. A hybridization probe comprising the polynucleotide sequence of claim 1.
3. An isolated and purified polynucleotide sequence comprising SEQ ID NO:2.
4. A polynucleotide sequence which is fully complementary to SEQ ID NO:2.
5. A hybridization probe comprising the polynucleotide sequence of claim 4.
6. An expression vector containing the polynucleotide sequence of claim 1.
7. A host cell line containing the expression vector of claim 6.
8. A method for producing a polypeptide comprising the amino acid sequence of SEQ ID NO:1, the method comprising the steps of:

a) culturing the host cell line of claim 7 under conditions suitable for the expression of the polypeptide; and
b) recovering the polypeptide from the host cell line culture.

* * * * *